(12) United States Patent
Soma et al.

(10) Patent No.: US 12,011,271 B2
(45) Date of Patent: Jun. 18, 2024

(54) ELECTRODE CATHETER

(71) Applicant: NIHON KOHDEN CORPORATION, Tokyo (JP)

(72) Inventors: Hirokazu Soma, Tokorozawa (JP); Nobuhiro Suzuki, Tokorozawa (JP); Kohei Nakamura, Tokorozawa (JP)

(73) Assignee: NIHON KOHDEN CORPORATION, Tokyo (JP)

(*) Notice: Subject to any disclaimer, the term of this patent is extended or adjusted under 35 U.S.C. 154(b) by 258 days.

(21) Appl. No.: 16/761,120

(22) PCT Filed: Nov. 1, 2018

(86) PCT No.: PCT/JP2018/040639
§ 371 (c)(1),
(2) Date: May 1, 2020

(87) PCT Pub. No.: WO2019/093213
PCT Pub. Date: May 16, 2019

(65) Prior Publication Data
US 2020/0275855 A1    Sep. 3, 2020

(30) Foreign Application Priority Data
Nov. 8, 2017  (JP) .............................. 2017-215638

(51) Int. Cl.
*A61B 5/28* (2021.01)
*A61B 5/00* (2006.01)
(Continued)

(52) U.S. Cl.
CPC .............. *A61B 5/287* (2021.01); *A61B 5/283* (2021.01); *A61B 5/6856* (2013.01); *A61B 2562/0209* (2013.01)

(58) Field of Classification Search
CPC .................. A61B 5/287; A61B 5/6856; A61B 2562/0209; A61B 5/283; A61B 5/6869; A61B 5/6852
(Continued)

(56) References Cited

U.S. PATENT DOCUMENTS 4,955,382 A * 9/1990 Franz .................... A61B 5/6855
600/375
5,398,683 A * 3/1995 Edwards ................ A61B 5/287
607/116
(Continued)

FOREIGN PATENT DOCUMENTS

| JP | 2001-292973 A | 10/2001 |
|---|---|---|
| JP | 2002-191571 A | 7/2002 |
| JP | 2016-524480 A | 8/2016 |

OTHER PUBLICATIONS

Japanese Office Action dated Jun. 8, 2021 issued in Patent Application No. 2017-215638.
(Continued)

*Primary Examiner* — Alexander Gilman
(74) *Attorney, Agent, or Firm* — Pearne & Gordon LLP (57) ABSTRACT

There is provided an electrode catheter for measuring an electric potential inside a heart of a subject. The electrode catheter includes: a shaft that is inserted into the heart, wherein the shaft includes a distal end portion, and a guide portion that is connected to the distal end portion; a non-contact electrode that is provided on an outer circumferential surface of the distal end portion or the guide portion; and at least one contact electrode that is provided on the outer circumferential surface of the distal end portion and that is configured to make contact with an endocardium of the heart. The non-contact electrode is provided on the outer circumferential surface of the distal end portion or the guide portion so as not to make contact with the endocardium in
(Continued)

a state where the contact electrode is in contact with the endocardium.

7 Claims, 8 Drawing Sheets

(51) Int. Cl.
 *A61B 5/283* (2021.01)
 *A61B 5/287* (2021.01)
(58) Field of Classification Search
 USPC ........................................................ 600/374
 See application file for complete search history.

(56) References Cited

U.S. PATENT DOCUMENTS

| | | | | |
|---|---|---|---|---|
| 5,423,878 | A * | 6/1995 | Franz | A61B 5/6855 |
| | | | | 607/122 |
| 5,445,148 | A * | 8/1995 | Jaraczewski | A61B 5/6855 |
| | | | | 600/374 |
| 5,476,495 | A * | 12/1995 | Kordis | A61B 5/287 |
| | | | | 600/374 |
| 5,562,619 | A * | 10/1996 | Mirarchi | A61M 25/0133 |
| | | | | 604/95.04 |
| 5,823,955 | A * | 10/1998 | Kuck | A61N 1/056 |
| | | | | 606/41 |
| 6,001,085 | A * | 12/1999 | Lurie | A61M 25/0054 |
| | | | | 604/524 |
| 6,241,724 | B1 * | 6/2001 | Fleischman | A61N 1/0565 |
| | | | | 606/41 |
| 6,301,496 | B1 * | 10/2001 | Reisfeld | G06T 17/20 |
| | | | | 600/407 |
| 6,892,091 | B1 * | 5/2005 | Ben-Haim | A61B 5/287 |
| | | | | 600/509 |
| 8,452,422 | B2 * | 5/2013 | Desinger | A61B 18/1492 |
| | | | | 607/154 |
| 9,636,164 | B2 * | 5/2017 | Panescu | A61B 5/01 |
| 9,993,178 | B2 * | 6/2018 | Panescu | A61B 17/00 |
| 10,973,436 | B2 * | 4/2021 | Kusumoto | A61B 34/20 |
| 11,020,180 | B2 * | 6/2021 | Viswanathan | A61B 18/1492 |
| 11,259,869 | B2 * | 3/2022 | Mickelsen | A61B 18/1492 |
| 11,350,815 | B2 * | 6/2022 | Rothe | A61B 1/0055 |
| 2007/0191709 | A1 * | 8/2007 | Swanson | A61N 1/0553 |
| | | | | 600/433 |
| 2012/0130368 | A1 * | 5/2012 | Jenson | A61B 18/1492 |
| | | | | 606/41 |
| 2014/0364715 | A1 * | 12/2014 | Hauck | A61B 5/063 |
| | | | | 606/34 |
| 2017/0274177 | A1 * | 9/2017 | Helgeson | A61M 25/0009 |
| 2019/0374120 | A1 | 12/2019 | Hauck | |
| 2020/0275855 | A1 * | 9/2020 | Soma | A61B 5/6856 |

OTHER PUBLICATIONS

International Search Report Issued in Patent Application No. PCT/JP2018/040639 dated Jan. 23, 2019.
Written Opinion Issued in Patent Application No. PCT/JP2018/040639 dated Jan. 23, 2019.

* cited by examiner

ELECTRODE CATHETER

TECHNICAL FIELD

The present disclosure relates to an electrode catheter. Particularly, the present disclosure relates to an electrode catheter for measuring an electric potential inside a heart of a patent.

BACKGROUND ART

JP-A-2002-191571 discloses an electrode catheter for measuring an electric potential inside a heart of a patient. According to the electrode catheter disclosed in JP-A-2002-191571, a plurality of ring electrodes are arranged side by side and provided on a distal end portion of a tube body, and a variation of the electric potential inside the heart can be measured by any of the plurality of ring electrodes (contact electrodes). While moving the electrode catheter, a medical worker carefully observes the variation of the electric potential inside the heart acquired from the electrode catheter. In this manner, the medical worker can estimate a place where arrhythmia (e.g. atrial fibrillation etc.) occurred inside the heart (e.g. inside a left atrium).

Each of the ring electrodes has to be in contact with an endocardium of the heart as a precondition for measuring the variation of the electric potential inside the heart using the electrode catheter. This is because an electric signal acquired from a predetermined ring electrode cannot reflect the variation of the electric potential inside the heart when the predetermined ring electrode is not in contact with the endocardium. Therefore, before observing the variation of the electric potential inside the heart (e.g. an electrocardiogram waveform) that is acquired from each of the ring electrodes and displayed on a monitor, the medical worker has to confirm whether the ring electrode is in contact with the endocardium or not. On the other hand, it is difficult for the medical worker to accurately determine whether the predetermined ring electrode is in contact with the endocardium or not by use of an X-ray fluoroscopic image of the patient.

To solve this problem, a method about how to determine contact between a predetermined ring electrode and the endocardium based on a variation of an impedance value between the ring electrode and an electrode attached to the patient has been under review. In this respect, since electric conductivity of blood is larger than electric conductivity of the endocardium, an impedance value measured by the ring electrode which has already been in contact with the endocardium is larger than an impedance value measured by the ring electrode which has not been in contact with the endocardium yet. It is however difficult to accurately determine the contact between the ring electrode and the endocardium when there is a small variation between the impedance value measured by the ring electrode which has already been in contact with the endocardium and the impedance value measured by the ring electrode which has not been in contact with the endocardium yet. From this viewpoint, there is still room for further improvement of usability of the electrode catheter.

SUMMARY OF INVENTION

The present disclosure provides an electrode catheter whose usability is improved.

According to one or more aspects of the present disclosure, there is provided an electrode catheter for measuring an electric potential inside a heart of a subject.

The electrode catheter comprises:
  a shaft that is inserted into the heart, wherein the shaft comprises a distal end portion, and a guide portion that is connected to the distal end portion;
  a non-contact electrode that is provided on an outer circumferential surface of the distal end portion or the guide portion; and
  at least one contact electrode that is provided on the outer circumferential surface of the distal end portion and that is configured to make contact with an endocardium of the heart.

The non-contact electrode is provided on the outer circumferential surface of the distal end portion or the guide portion so as not to make contact with the endocardium in a state where the contact electrode is in contact with the endocardium.

DESCRIPTION OF EMBODIMENT

An embodiment of the present invention (hereinafter referred to as present embodiment) will be described below with reference to the drawings. Incidentally, description about members having the same reference signs as those of members that have already been described in description of the present embodiment will be omitted for convenience of explanation. In addition, in some cases, dimensions of each member shown in the drawings may be different from actual dimensions of the member for convenience of explanation.

Figure 1:
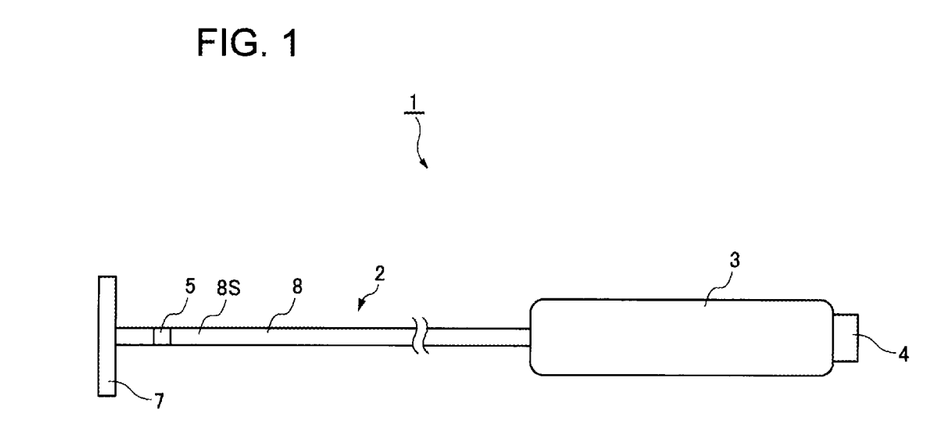
FIG. 1 is an overall view of an electrode catheter according to an embodiment of the present invention (hereinafter referred to as present embodiment simply).

FIG. 1 shows an overall view of an electrode catheter 1 according to the present embodiment. As shown in FIG. 1, the electrode catheter 1 is provided with a shaft 2, a handle 3, and a connector 4. The electrode catheter 1 is configured to measure an electric potential (particularly a variation of an electric potential) inside a heart of a subject (e.g. a patient). After inserting the shaft 2 into the heart of the subject, a medical worker carefully observes the variation of the electric potential inside the heart acquired from the electrode catheter 1 while moving the shaft 2 inside the heart. In this manner, the medical worker can estimate a place where arrhythmia (e.g. atrial fibrillation etc.) occurred inside the heart (e.g. inside a left atrium). Here, an electrocardiogram waveform indicating the variation of the electric potential inside the heart over time is generated based on an electric signal acquired from the shaft 2, and displayed on a not-shown display device.

The shaft 2 is configured to be inserted into the heart. The shaft 2 is configured, for example, by a hollow flexible tube, and has a distal end portion 7 and a guide portion 8. The shaft 2 is formed, for example, out of a resin material. The distal end portion 7 is configured to make contact with an endocardium of the subject. Particularly, the distal end portion 7 is formed into a planar shape (e.g. a ring shape) in order to configure a contact surface for making contact with the endocardium (see FIG. 2). The guide portion 8 is connected to the distal end portion 7 and configured integrally with the distal end portion 7. An extension direction of the distal end portion 7 and an extension direction of the guide portion 8 are different from each other. In this respect, the distal end portion 7 and the guide portion 8 may be perpendicular to each other, or an angle formed by the distal end portion 7 and the guide portion 8 may be set within a range of from 70° to 110° in a used state in which the distal end portion 7 contacts the endocardium. In addition, the extension direction of the distal end portion 7 and the extension direction of the guide portion 8 may be the same as each other in a state before the distal end portion 7 contacts the endocardium. In this case, in a state in which the distal end portion 7 contacts the endocardium, the distal end portion 7 may be deformed such that the extension direction of the distal end portion 7 and the extension direction of the guide portion 8 are different from each other.

The handle 3 can be operated by the medical worker. The medical worker who operates a predetermined operating portion (not shown) provided in the handle 3 can control the guide portion 8 of the shaft 2 to bend. Particularly, the guide portion 8 has a bendable portion 20 (see FIG. 5B) configured to bend in accordance with the operation of the medical worker. The connector 4 is configured to connect the electrode catheter 1 to an input amplifier device (not shown). An electric signal indicating a variation of an electric potential inside the heart acquired by the electrode catheter 1 is inputted to the input amplifier device through the connector 4.

Figure 2:
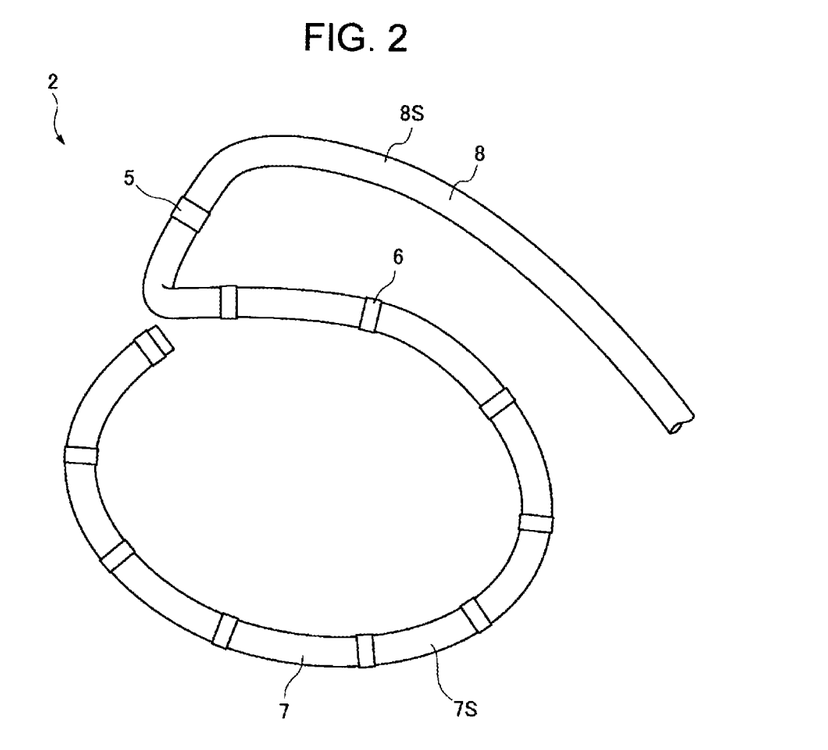
FIG. 2 is a perspective view showing a distal end portion and a guide portion of a shaft.
Figure 3A:
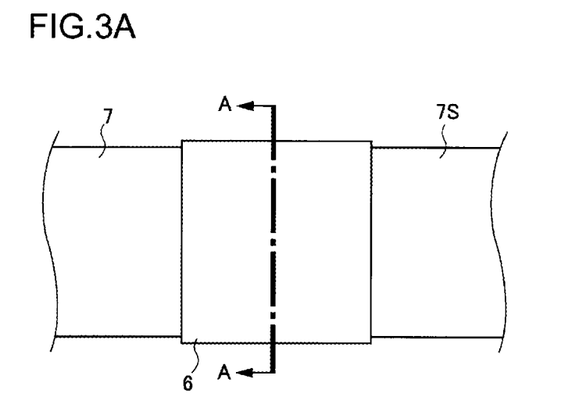
FIG. 3A is a side view showing a part of the distal end portion of the shaft of the electrode catheter in an enlarged manner.
Figure 3B:
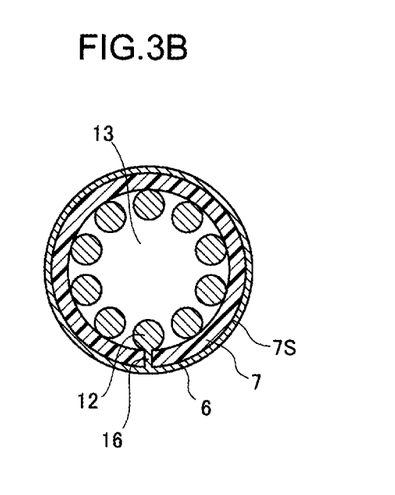
FIG. 3B is a sectional view of the distal end portion of the shaft of the electrode catheter cut along a line A-A shown in FIG. 3A.

Next, a specific configuration of the distal end portion 7 of the shaft 2 will be described with reference to FIG. 2 and FIGS. 3A and 3B. FIG. 2 is a perspective view showing the distal end portion 7 and the guide portion 8. FIG. 3A is a side view showing a part of the distal end portion 7 in an enlarged manner. FIG. 3B is a sectional view of the distal end portion 7 cut along a line A-A shown in FIG. 3A.

As shown in FIG. 2 and FIGS. 3A and 3B, the electrode catheter 1 is provided with a plurality of ring electrodes 6 (an example of contact electrodes), and one non-contact electrode 5. The plurality of ring electrodes 6 are configured to make contact with the endocardium of the heart of the subject. The plurality of ring electrodes 6 are provided to surround an outer circumferential surface 7S of the distal end portion 7, and disposed along the extension direction of the distal end portion 7 so as to be separated from one another. The ring electrodes 6 are formed out of an electrically conductive material. For example, the ring electrodes 6 may be formed out of platinum or an alloy of platinum and iridium. The non-contact electrode 5 (also referred to as reference electrode) is provided on an outer circumferential surface 8S of the guide portion 8 so as to surround the outer circumferential surface 8S. Particularly, the non-contact electrode 5 is provided on the outer circumferential surface 8S of the guide portion 8 so as not to make contact with the endocardium in a state in which the ring electrodes 6 are in contact with the endocardium. The non-contact electrode 5 is formed out of an electrically conductive material. For example, the non-contact electrode 5 may be formed out of platinum or an alloy of platinum and iridium. Particularly, the ring electrodes 6 and the non-contact electrode 5 may be formed out of the same material. Further, the surface area of the non-contact electrode 5 may be substantially equal to the surface area of each of the ring electrodes 6. Incidentally, in the present embodiment, ten ring electrodes 6 are provided on the outer circumferential surface 7S of the distal end portion 7. However, the number of the ring electrodes 6 is not limited particularly. For example, the number of the ring electrodes 6 provided on the outer circumferential surface 7S may be one.

In addition, as shown in FIG. 3B, the electrode catheter 1 is further provided with a plurality of electric wires 12 provided in a hollow portion 13 of the shaft 2. Each of the electric wires 12 extends along an extension direction of the shaft 2. Each of the electric wires 12 is electrically connected to a corresponding one of the ring electrodes 6 through a connection conductor 16 provided inside the distal end portion 7 of the shaft 2. An electric signal indicating a variation of an intracardiac electric potential over time is inputted from the ring electrode 6 to the input amplifier device through the electric wire 12 and the connector 4. For example, after amplifying a difference between an electric signal acquired by a predetermined ring electrode 6 and an electric signal acquired by another ring electrode 6 different from the predetermined ring electrode 6, the input amplifier device applies analog-to-digital conversion to the amplified difference between the electric signals. In this manner, the input amplifier device can generate data of an electrocardiogram waveform indicating a variation of a voltage between any two ring electrodes 6 in combination over time. In addition, the non-contact electrode 5 is electrically connected to a corresponding one of the electric wires 12 through a connection conductor 16 provided in the guide portion 8 of the shaft 2.

In addition, an operating wire (not shown) configured to bend the guide portion 8 of the shaft 2 may be provided in the hollow portion 13. When the operating wire bends in accordance with an operation performed on the handle 3 (see FIG. 1) by the medical worker, a part of the guide portion 8 bends (see FIG. 5B). In addition, the hollow portion 13 may be filled with an insulating material so that the electric wires 12 can be embedded therein.

Figure 4:
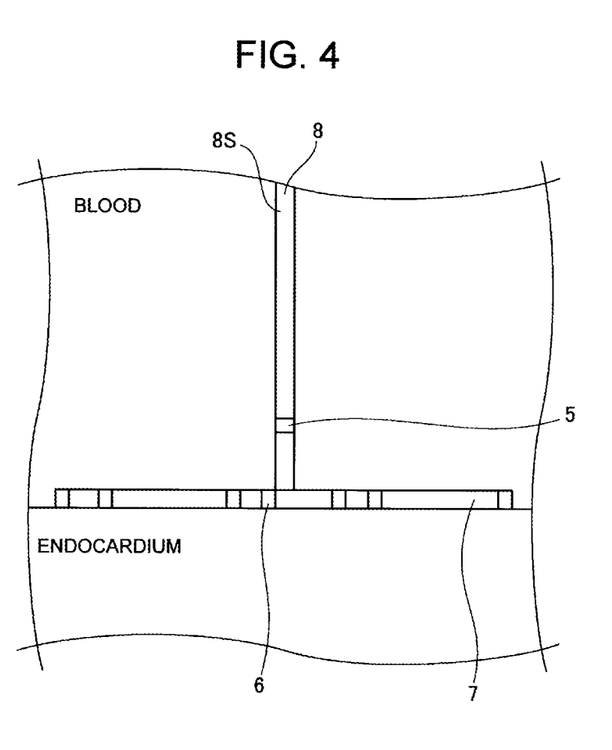
FIG. 4 is a view showing a state in which ring electrodes are in contact with an endocardium.

Next, a method for comparing an impedance value between each of the ring electrodes 6 and an impedance measuring electrode attached to a part (e.g. the back etc.) of a body of the subject, with an impedance value between the non-contact electrode 5 and the impedance measuring electrode to thereby determine contact between the ring electrode 6 and the endocardium will be described with reference to FIG. 4. FIG. 4 is a view showing a state in which the plurality of ring electrodes 6 are in contact with the endocardium.

Incidentally, the impedance measuring electrode may be attached to the body surface of the back etc. of the subject, or may be placed inside the body of the subject. In this respect, one of the ring electrodes 6 may function as the impedance measuring electrode. In addition, the impedance measuring electrode may be connected to the ground. In addition, the impedance value indicates the amplitude of impedance. The impedance value relevant to the ring electrode 6 may be measured based on a value of an AC voltage of a predetermined frequency applied to the ring electrode 6 and a current value outputted from the ring electrode 6. In addition, the impedance value relevant to the non-contact electrode 5 may be measured based on the value of the AC voltage of the predetermined frequency applied to the non-contact electrode 5 and a current value outputted from the non-contact electrode 5. Further, assume that each of the ring electrodes 6 and the non-contact electrode 5 are formed out of the same material, and the surface area of the non-contact electrode 5 is substantially equal to the surface area of the ring electrode 6.

First, description will be made about a state in which each of the ring electrodes 6 is not in contact with the endocardium. In this state, the surface of the ring electrode 6 makes contact with only blood. Therefore, an impedance value between the ring electrode 6 and the impedance measuring electrode is mainly determined based on electric conductivity $\alpha 1$ of the blood. On the other hand, the surface of the non-contact electrode 5 also makes contact with only the blood. Therefore, an impedance value between the non-contact electrode 5 and the impedance measuring electrode is also mainly determined based on the electric conductivity $\alpha 1$ of the blood. Thus, in the state in which each of the ring electrodes 6 is not in contact with the endocardium, the impedance value between the ring electrode 6 and the impedance measuring electrode is substantially equal to the impedance value between the non-contact electrode 5 and the impedance measuring electrode, or a difference between the two impedance values is small.

Next, in a state in which each of the ring electrodes 6 is in contact with the endocardium, as shown in FIG. 4, the surface of the ring electrode 6 makes contact with both the blood and the endocardium. Therefore, an impedance value between the ring electrode 6 and the impedance measuring electrode is mainly determined based on the electric conductivity $\alpha 1$ of the blood and electric conductivity $\alpha 2$ of the endocardium. On the other hand, the surface of the non-contact electrode 5 makes contact with only the blood. Therefore, an impedance value between the non-contact electrode 5 and the impedance measuring electrode is mainly determined based on the electric conductivity $\alpha 1$ of the blood. Thus, in the state in which each of the ring electrodes 6 is in contact with the endocardium, the impedance value between the ring electrode 6 and the impedance measuring electrode is largely different from the impedance value between the non-contact electrode 5 and the impedance measuring electrode.

According to the present embodiment, the non-contact electrode 5 does not make contact with the endocardium even in the state in which each of the ring electrodes 6 is in contact with the endocardium (the state shown in FIG. 4). Therefore, by comparing the impedance value between the ring electrode 6 and the impedance measuring electrode (the impedance value relevant to the ring electrode 6) with the impedance value between the non-contact electrode 5 and the impedance measuring electrode (the impedance value relevant to the non-contact electrode 5), it is possible to accurately determine whether the ring electrode 6 is in contact with the endocardium or not. Specifically, when a difference between the impedance value relevant to the ring electrode 6 and the impedance value relevant to the non-contact electrode 5 is smaller than a predetermined threshold, it is possible to determine that the ring electrode 6 is not in contact with the endocardium. On the other hand, when the difference between the impedance value relevant to the ring electrode 6 and the impedance value relevant to the non-contact electrode 5 is not smaller than the predetermined threshold, it is possible to determine that the ring electrode 6 is in contact with the endocardium.

Accordingly, by referring to the impedance value relevant to the non-contact electrode 5, it is possible to accurately determine whether the ring electrode 6 is in contact with the endocardium or not. Accordingly, it is possible to accurately measure a variation of an electric potential inside the heart (e.g. inside the left atrium) of the subject. Thus, it is possible to provide the electrode catheter 1 whose usability is improved.

Particularly, in the present embodiment, it is possible to accurately determine whether the ring electrode 6 is in contact with the endocardium or not, without moving the distal end portion 7 of the shaft 2 but with the distal end portion 7 kept in a still state as it is.

Incidentally, determination about the contact between the ring electrode 6 and the endocardium based on the comparison between the impedance value relevant to the ring electrode 6 and the impedance value relevant to the non-contact electrode 5 may be automatically made by a computer (a processor such as a CPU) communicably connected to the electrode catheter 1. In this case, the computer may acquire the impedance value relevant to the ring electrode 6 and the impedance value relevant to the non-contact electrode 5 from the electrode catheter 1, and then automatically determine the contact between the ring electrode 6 and the endocardium based on the acquired impedance values and a contact determination program. Alternatively, the contact determination may be subjectively made by the medical worker operating the electrode catheter 1. In this case, the medical worker may visually recognize the impedance value relevant to the ring electrode 6 and the impedance value relevant to the non-contact electrode 5 displayed on the display device (not shown) to thereby subjectively determine the contact between the ring electrode 6 and the endocardium.

In addition, according to the present embodiment, the ring electrodes 6 can make contact with the endocardium simultaneously. Accordingly, it is possible to simultaneously measure variations of intracardiac electric potentials corresponding to the ring electrodes 6 respectively. Further, since the extension direction of the distal end portion 7 of the shaft 2 and the extension direction of the guide portion 8 of the shaft 2 are different from each other, it is possible to increase a contact area between the distal end portion 7 and the endocardium. Accordingly, it is possible to increase the number of the ring electrodes 6 capable of making contact with the endocardium simultaneously. Further, in a state in which the ring electrodes 6 provided on the outer circumferential surface 7S of the distal end portion 7 are in contact with the endocardium, the non-contact electrode 5 provided on the outer circumferential surface 8S of the guide portion 8 can be surely prevented from making contact with the endocardium.

In addition, according to the present embodiment, each of the ring electrodes 6 and the non-contact electrode 5 are formed out of the same material, and the surface area of the non-contact electrode 5 is substantially equal to the surface area of the ring electrode 6. Therefore, in the state in which the ring electrode 6 is not in contact with the endocardium, the impedance value relevant to the ring electrode 6 and the impedance value relevant to the non-contact electrode 5 are substantially equal to each other. Therefore, when the difference between the two impedance values is small (particularly close to zero), it is possible to determine that the ring electrode 6 is not in contact with the endocardium. On the other hand, when the difference between the two impedance values is large, it is possible to determine that the ring electrode 6 is in contact with the endocardium. Incidentally, the non-contact electrode 5 may be formed out of an electrically conductive material different from that of the ring electrode 6 or the surface area of the non-contact electrode 5 may be different from the surface area of the ring electrode 6. In this respect, for example, assume that, the impedance value relevant to the ring electrode 6 is Z1 and the impedance value relevant to the non-contact electrode 5 is Z2 (Z1≠Z2) in the state in which the ring electrode 6 is not in contact with the endocardium. In this case, when a difference ΔZ between the impedance value relevant to the ring electrode 6 and the impedance value relevant to the non-contact electrode 5 is a value close to (Z2−Z1), it is possible to determine that the ring electrode 6 is not in contact with the endocardium. On the other hand, when the difference ΔZ between the impedance value relevant to the ring electrode 6 and the impedance value relevant to the non-contact electrode 5 is a value far from (Z2−Z1), it is possible to determine that the ring electrode 6 is in contact with the endocardium.

Figure 5A:
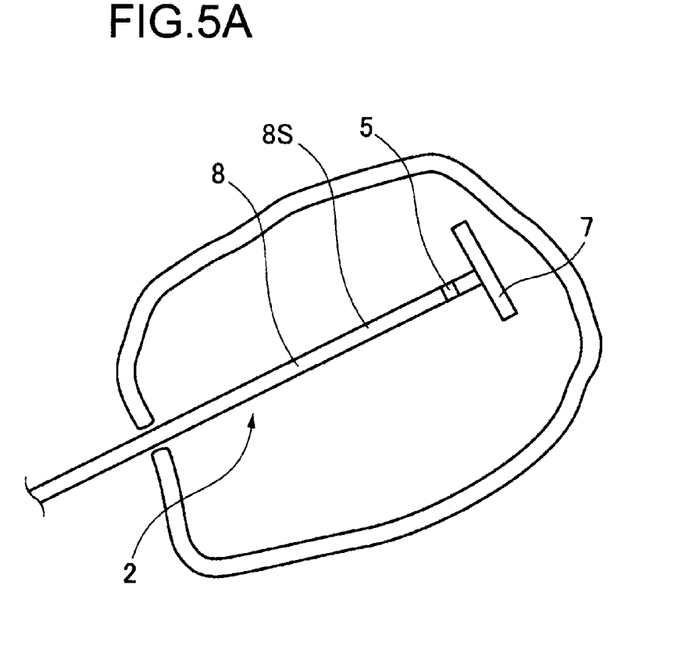
FIG. 5A is a view showing a state in which the shaft inserted into a left atrium has not bent yet.
Figure 5B:
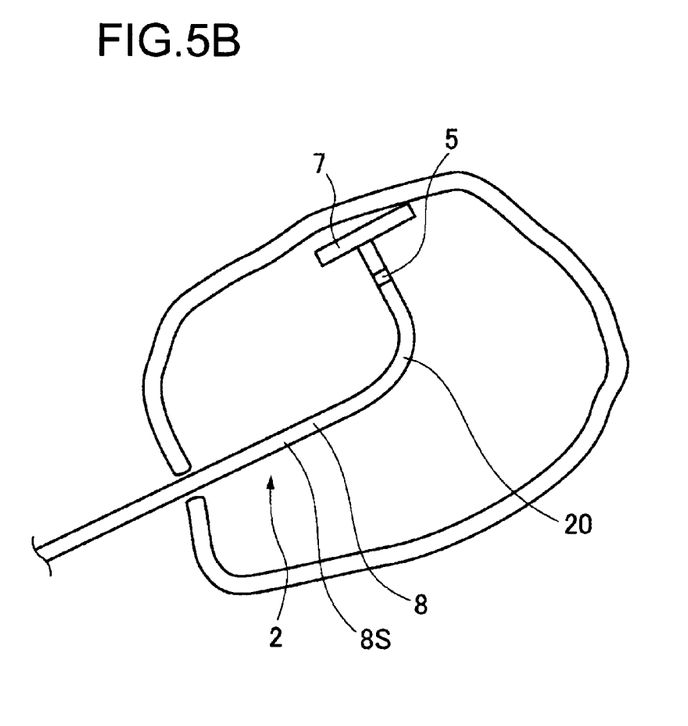
FIG. 5B is a view showing a state in which the shaft inserted into the left atrium has already bent.

Next, a placement position of the non-contact electrode 5 will be described with reference to FIGS. 5A and 5B. FIG. 5A is a view showing a state in which the shaft 2 inserted into the left atrium has not bent yet. FIG. 5B is a view showing a state in which the shaft 2 inserted into the left atrium has already bent. As shown in FIGS. 5A and 5B, the non-contact electrode 5 is provided on the outer circumferential surface 8S of the guide portion 8. Particularly, in consideration of the fact that an upper limit value of the diameter of a normal left atrium of a general adult is 40 mm, it is preferable that the non-contact electrode 5 is provided on the outer circumferential surface 8S of the guide portion 8 so that a distance between a boundary between the distal end portion 7 and the guide portion 8 and the non-contact electrode 5 is not longer than 40 mm. In this respect, when the distance between the distal end portion 7 and the non-contact electrode 5 is not longer than 40 mm, as shown in FIG. 5A, it is possible to surely prevent contact between the non-contact electrode 5 and the endocardium in the state in which the ring electrodes 6 are in contact with the endocardium. Further, it is more preferable that the non-contact electrode 5 is provided on the outer circumferential surface 8S of the guide portion 8 between the distal end portion 7 and the bendable portion 20, as shown in FIG. 5B. Also in the case, it is possible to surely prevent contact between the non-contact electrode 5 and the endocardium in the state in which the ring electrodes 6 are in contact with the endocardium.

(Modification)

Figure 6:
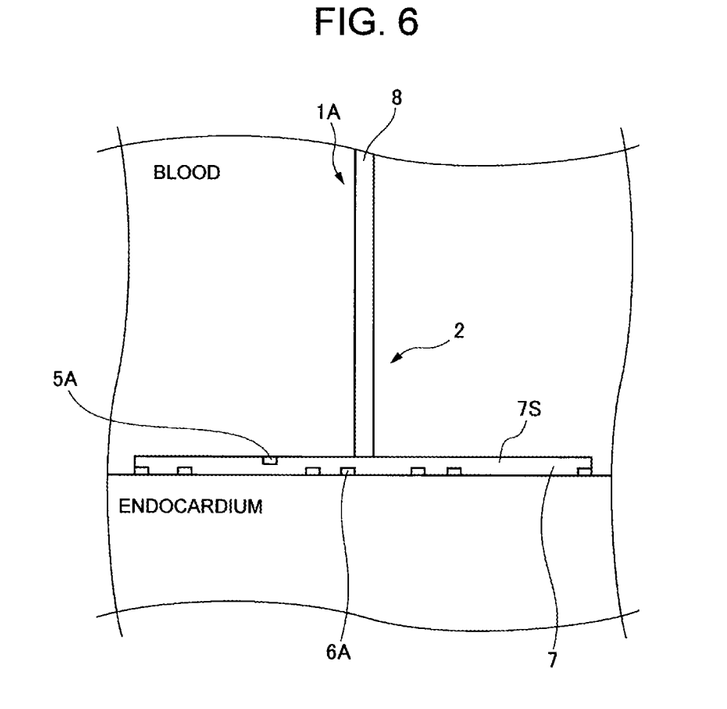
FIG. 6 is a view showing a shaft of an electrode catheter according to a modification of the present embodiment.
Figure 7A:
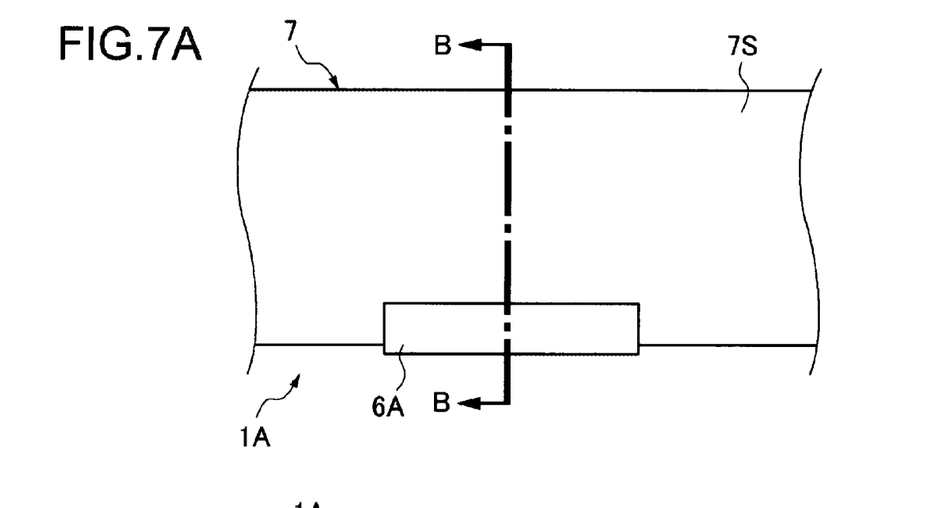
FIG. 7A is a side view showing a part of a distal end portion of the shaft of the electrode catheter according to the modification in an enlarged manner.
Figure 7B:
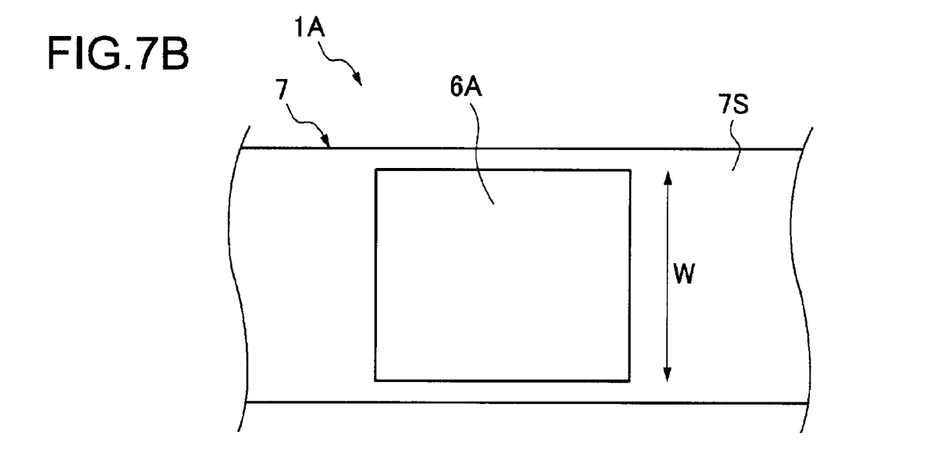
FIG. 7B is a plan view showing the part of the distal end portion of the shaft of the electrode catheter according to the modification in the enlarged manner.
Figure 7C:
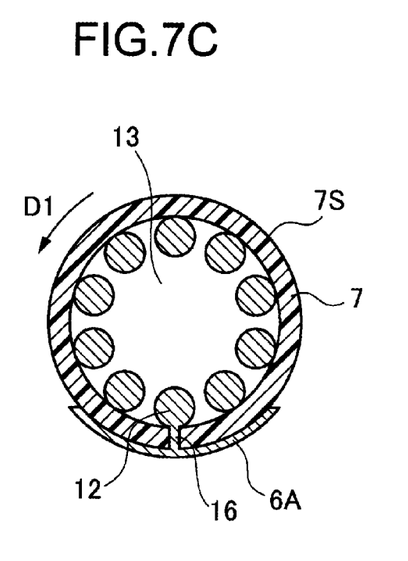
FIG. 7C is a sectional view of the distal end portion of the shaft of the electrode catheter according to the modification cut along a line B-B shown in FIG. 7A.

Next, an electrode catheter 1A according to a modification of the present embodiment will be described below with reference to FIG. 6 and FIGS. 7A to 7C. In the present modification, members having the same reference signs as those of members that have already been described in the description of the present embodiment will be omitted for convenience of explanation. FIG. 6 is a view showing a shaft 2 of the electrode catheter 1A according to the present modification. FIG. 7A is a side view showing a part of a distal end portion 7 in an enlarged manner. FIG. 7B is a plan view showing the part of the distal end portion 7 in the enlarged manner. FIG. 7C is a sectional view of the distal end portion 7 cut along a line B-B shown in FIG. 7A.

The electrode catheter 1A according to the present modification differs from the electrode catheter 1 according to the present embodiment at the point that a plurality of chip electrodes 6A (an example of contact electrodes) are provided in place of the plurality of ring electrodes 6. As shown in FIG. 6 and FIGS. 7A to 7C, each of the chip electrodes 6A is provided on an outer circumferential surface 7S of the distal end portion 7 of the shaft 2, and configured to make contact with an endocardium. The number of the chip electrodes 6A provided on the outer circumferential surface 7S is, for example, 10. However, the number of the chip electrodes 6A is not limited particularly. The plurality of chip electrodes 6A are disposed along an extension direction of the distal end portion 7 so as to be separated from one another. The chip electrodes 6A may be formed out of the same electrically conductive material as the ring electrodes 6 according to the present embodiment. For example, the chip electrodes 6A may be formed out of platinum or an alloy of platinum and iridium. In addition, a dimension W of each of the chip electrodes 6A extending along an outer circumference direction D1 (see FIG. 7C) of the distal end portion 7 is smaller than a circumferential length of the distal end portion 7. Here, the circumferential length of the distal end portion 7 is a value obtained by multiplying an outer diameter of the distal end portion 7 by π. Particularly, it is preferable that the dimension W of the chip electrode 6A extending along the outer circumference direction D1 of the distal end portion 7 is not larger than 50% of the circumferential length of the distal end portion 7.

In addition, the respective chip electrodes 6A make contact with the endocardium of a heart simultaneously in the state in which the distal end portion 7 is in contact with the endocardium. In other words, the chip electrodes 6A are positioned on the outer circumferential surface 7S of the distal end portion 7 making contact with the endocardium. Each of the chip electrodes 6A is electrically connected to a corresponding one of electric wires 12 through a connection conductor 16. The electric wires 12 are provided in a hollow portion 13 of the shaft 2.

In addition, as shown in FIG. 6, a non-contact electrode 5A is provided on the outer circumferential surface 7S of the distal end portion 7. Particularly, the non-contact electrode 5A is provided on the outer circumferential surface 7S not making contact with the endocardium (in other words, the outer circumferential surface not facing the endocardium). Therefore, the non-contact electrode 5A does not make contact with the endocardium in the state in which the chip electrodes 6A are in contact with the endocardium. The non-contact electrode 5A is formed out of an electrically conductive material. For example, the non-contact electrode 5A may be formed out of platinum or an alloy of platinum and iridium. Particularly, the chip electrodes 6A and the non-contact electrode 5A may be formed out of the same material. Further, the surface area of the non-contact electrode 5A may be substantially equal to the surface area of each of the chip electrodes 6A. In addition, the non-contact electrode 5A is electrically connected to a corresponding one of the electric wires 12 through a connection conductor 16 provided inside the distal end portion 7.

According to the present modification, the non-contact electrode 5A does not make contact with the endocardium in the state in which each of the chip electrodes 6A is in contact with the endocardium (the state shown in FIG. 6). Therefore, by comparing an impedance value between the chip electrode 6A and an impedance measuring electrode (an impedance value relevant to the chip electrode 6A) with an impedance value between the non-contact electrode 5A and the impedance measuring electrode (an impedance value relevant to the non-contact electrode 5A), it is possible to accurately determine whether the chip electrode 6A is in contact with the endocardium or not. Specifically, when a difference between the impedance value relevant to the chip electrode 6A and the impedance value relevant to the non-contact electrode 5A is smaller than a predetermined threshold, it is possible to determine that the chip electrode 6A is not in contact with the endocardium. On the other hand, when the difference between the impedance value relevant to the chip electrode 6A and the impedance value relevant to the non-contact electrode 5A is not smaller than the predetermined threshold, it is possible to determine that the chip electrode 6A is in contact with the endocardium.

Accordingly, by referring to the impedance value relevant to the non-contact electrode 5A, it is possible to accurately determine whether the chip electrode 6A is in contact with the endocardium or not. Accordingly, it is possible to accurately measure a variation of an electric potential inside the heart (e.g. inside a left atrium) of the subject. Thus, it is possible to provide the electrode catheter 1A whose usability is improved. Particularly, in the present modification, it is possible to accurately determine whether the chip electrode 6A is in contact with the endocardium or not, without moving the distal end portion 7 of the shaft 2 but with the distal end portion 7 kept in a still state as it is.

Although the embodiment of the present invention has been described above, the technical scope of the present invention should not be interpreted limitedly based on the description of the present embodiment. The present embodiment is merely exemplified. It should be understood by those skilled in the art that various changes can be made on the embodiment within the scopes of the claimed inventions. The technical scopes of the claimed inventions should be defined based on the scope of the claims and its equivalent scope.

For example, in the present embodiment, the distal end portion 7 of the shaft 2 is formed into a ring shape to have the contact surface for making contact with the endocardium. However, the shape of the distal end portion 7 is not limited thereto. For example, the distal end portion 7 may be formed into a radial shape, a hexagonal shape or a spiral shape.

This application is based on Japanese Patent Application No. 2017-215638 filed on Nov. 8, 2017, the entire contents of which are incorporated herein by reference.

The invention claimed is:

1. An electrode catheter for measuring an electric potential inside a heart of a subject, the electrode catheter comprising:
a shaft that is inserted into the heart, wherein the shaft comprises a distal end portion, and a guide portion that is connected to the distal end portion;
a non-contact electrode that is provided on an outer circumferential surface of the guide portion; and
at least one contact electrode that is provided on the outer circumferential surface of the distal end portion and that is configured to make contact with an endocardium of the heart,
wherein the non-contact electrode is provided on the outer circumferential surface of the guide portion so as not to make contact with the endocardium in a state where the contact electrode is in contact with the endocardium,
wherein the distal end portion has a predetermined shape different from a shape of the guide portion, and
a first impedance value related to the non-contact electrode and a second impedance value related to the contact electrode are provided to a computer configured to compare the first impedance value and the second impedance value, or to a display device configured to display the first impedance value and the second impedance value.

2. The electrode catheter according to claim 1, wherein the guide portion comprises a bendable portion that is configured to bend in accordance with an operation of an operator, and the non-contact electrode is formed on the outer circumferential surface of the guide portion between the distal end portion and the bendable portion.

3. The electrode catheter according to claim 1, wherein a distance between the non-contact electrode and a boundary between the distal end portion and the guide portion is not longer than 40 mm.

4. The electrode catheter according to claim 1, wherein the non-contact electrode is provided on the outer circumferential surface of the distal end portion not facing the endocardium.

5. The electrode catheter according to claim 1, wherein the contact electrode and the non-contact electrode are formed of the same material, and a surface area of the non-contact electrode is substantially equal to a surface area of the contact electrode.

6. The electrode catheter according to claim 1, wherein an extension direction of the distal end portion and an extension direction of the guide portion are different from each other.

7. An electrode catheter for measuring an electric potential inside a heart of a subject, the electrode catheter comprising:
a shaft that is inserted into the heart, wherein the shaft comprises a distal end portion, and a guide portion that is connected to the distal end portion;
a non-contact electrode that is provided on an outer circumferential surface of the guide portion; and
at least one contact electrode that is provided on the outer circumferential surface of the distal end portion and that is configured to make contact with an endocardium of the heart,
wherein the non-contact electrode is provided on the outer circumferential surface of the guide portion so as not to make contact with the endocardium in a state where the contact electrode is in contact with the endocardium,
wherein the distal end portion has a ring shape that is different from a shape of the guide portion, and
a first impedance value related to the non-contact electrode and a second impedance value related to the contact electrode are provided to a computer configured to compare the first impedance value and the second impedance value, or to a display device configured to display the first impedance value and the second impedance value.

* * * * *